United States Patent [19]
Joshi et al.

[11] Patent Number: 5,593,552
[45] Date of Patent: Jan. 14, 1997

[54] DEVICE FOR ELECTROCHEMICAL GENERATION OF GAS

[75] Inventors: Ashok V. Joshi; John H. Gordon, both of Salt Lake City, Utah

[73] Assignee: Ceramatec, Inc., Salt Lake City, Utah

[21] Appl. No.: 413,635

[22] Filed: Mar. 30, 1995

Related U.S. Application Data

[63] Continuation-in-part of Ser. No. 58,438, May 7, 1993, Pat. No. 5,454,922, and a continuation-in-part of Ser. No. 204, 026, Feb. 28, 1994.

[51] Int. Cl.⁶ .............................. C25B 9/00; C25B 15/00
[52] U.S. Cl. ...................... 204/228; 204/265; 204/266
[58] Field of Search ............................... 204/228, 265, 204/266

[56] References Cited

U.S. PATENT DOCUMENTS

| | | | |
|---|---|---|---|
| 3,957,617 | 5/1976 | Aber et al. | 204/228 X |
| 4,169,775 | 10/1979 | Kuo | 204/228 X |
| 4,789,448 | 12/1988 | Woodhouse | 204/228 |
| 5,186,805 | 2/1993 | Gross et al. | 204/265 |
| 5,372,691 | 12/1994 | Kao et al. | 204/265 |
| 5,378,337 | 1/1995 | Kiyomura | 204/228 |

*Primary Examiner*—Donald R. Valentine
*Attorney, Agent, or Firm*—Trask, Britt & Rossa

[57] ABSTRACT

A device for generating controlled quantities of gas at predictable rates from an electrochemical cell containing a decomposable metal carbonate, bicarbonate or basic carbonate is disclosed. The cell provides more than one molecule of gas from the anode per 4 electrons passing through the cell circuit. The generated gas is comprised of carbon dioxide or a mixture of carbon dioxide and oxygen.

27 Claims, 6 Drawing Sheets

$O_2 + CO_2$ $O_2 + CO_2$

DEVICE FOR ELECTROCHEMICAL GENERATION OF GAS

This is a continuation-in-part of prior U.S. application Ser. No. 08/058,438, filed May 7, 1993 now U.S. Pat. No. 5,454,922 and Ser. No. 08/204,026 filed Feb. 28, 1994.

BACKGROUND OF INVENTION

Related Applications: This is a continuation-in-part of U.S. applications Ser. No. 08/058,438 which was filed May 7, 1993 now U.S. Pat. No. 5,454,922 and Ser. No. 08/204,026 which was filed Feb. 28, 1994 both having common inventors and assigned to the same assignee as the instant application.

Field: This invention relates to self-contained, gas-generating devices useful to displace fluids from a fluid repository to dispense said fluids preferable at a predictable flow rate.

State of the Art: A number of devices have been proposed for fluid delivery via gas generation.

Fluid generation at controlled rates is desired for drug delivery purposes, such as in implantable devices. Fluid generation may also be desirable where fragrant liquids, insecticides, or disinfectants are to be dispensed.

Exemplary of devices utilized for gas generation are U.S. Pat. No. 3,894,538 (Richter), U.S. Pat. No. 4,522,698 and U.S. Pat. No. 4,902,278 (Maget), also U.S. Pat. No. 5,242,565 (Winsel).

Electrochemically generating gases at electrodes is well known in the prior art.

Richter in U.S. Pat. No. 3,894,538 describes how a gas generated electrolytically can be used to increase the volume in a compartment which shares a flexible wall with a second compartment containing fluid to be dispensed. Thus electrolytically generated gas could be used to drive a dispensing device.

LaConti et al. in U.S. Pat. No. 4,039,409 describes a method for electrochemically pumping oxygen across a cation exchange membrane. Oxygen gas is released at the anode. According to the invention, one molecule of oxygen gas is released for every four electrons passing through an electric circuit.

Maget et al. has several patents, U.S. Pat. Nos. 4,522,698, 4,902,278, 4,402,817 which employ the general principles disclosed by Richter. In these disclosures, between one and two molecules are evolved at an electrode and are available for pumping per four electrons.

Winsel in U.S. Pat. No. 5,242,565 describes a device for electrochemically generating only a hydrogen gas from a Zn/air battery discharged in the absence of oxygen gas, or, alternatively, a device which decomposes a reducible oxide or nitrate to generate only oxygen. In practice, maintaining an oxygen-free condition to generate hydrogen is very difficult. Generation of oxygen via a Winsel device requires four electrons of current for every oxygen molecule generated.

Michel et al., U.S. Pat. No. 4,969,874 discloses a system similar to that of Winsel wherein a gas-generating electrochemical cell is utilized to drive the plunger of a syringe.

SUMMARY OF THE INVENTION

The novel electrochemical cell of the instant invention is particularly useful for producing a predetermined quantity of gas at a predictable rate via electrolytic decomposition of a carbonate or bicarbonate containing chemical in a coulombically efficient manner. The cell has an anode which is, in part, composed of the carbonate or bicarbonate chemical, also a cathode, an ionically permeable separator or cation conducting membrane separating the anode from the cathode but enabling ionic conduction from one to the other.

Prior art means for electrochemically evolving a non-reactive mixture of gas generally produce no more than two molecules of gas per four electrons. The present invention, in contrast, provides a means for electrochemically evolving up to five molecules of gas at a single electrode per four electrons involved in the electrochemical reaction. Thus, the present invention electrochemically generates gas more efficiently from a coulombic viewpoint than other systems known in the prior art. Such efficiency is a major advantage when utilizing a battery to drive the current flow through the cell. The increased efficiency enables the utilization of batteries with lower capacity to drive pumping of the same amount of fluid when the gas generating cell is coupled to a fluid dispensing reservoir.

Unlike the reactive mixture obtained when oxygen and hydrogen gasses are collected from electrolyzed water, the instant invention provides a mixture of oxygen and carbon dioxide which is unreactive. Devices incorporating the instant invention may also be combined with an oxygen scavenger so that the evolved gas contains substantially only carbon dioxide. Such a gas stream may be preferred when fluid delivery is required but there is concern regarding oxidation of any active material being delivered or of the environment of the device.

Particularly useful devices of the instant invention include micro-devices powered by micro-batteries similar to those used in hearing aids. While very small volumes of gas are produced using the devices of the instant invention, the high coulombic efficiency is very desirable since miniature batteries can be successfully used. The devices are useful also for other than micro volumetric purposes.

In some embodiments of the present invention, the anode contains an electrolytically-decomposable metal carbonate, such as sodium carbonate, wherein the metal ion is transportable through a properly-selected solid, non-porous electrolyte, and the carbonate forms oxygen and carbon dioxide gases as electrons are released. Water or other polar solvent for the carbonate or bicarbonate is generally also present in the anode.

The anode reaction is:

1) $M_2CO_3 \rightarrow 2M^+ + CO_2 + \frac{1}{2}O_2 + 2e^-$; where $M^+$ is a monovalent metal ion.

For the cathode reaction there are several possibilities which each have an advantage. In one case, the cathode includes water which decomposes to hydrogen gas and hydroxyl ions. Typically, a small quantity of a metal hydroxide, e.g., NaOH, is present to enhance the conductivity of the cathode.

The cathode reaction is:

2a) $2H_2O + 2e^- \rightarrow H_2 + 2OH^-$, or $2M^+ + 2H_2O + 2e^- \rightarrow H_2 + 2MOH$ The ion $M^+$ in the cathode comes from the anode, being transported through the electrolyte to the cathode. The overall reaction is:

2b) $M_2CO_3 + 2H_2O \rightarrow 2MOH + CO_2 + \frac{1}{2}O_2 + H_2$

Examples of the carbonates preferably include sodium carbonate and potassium carbonate, although other useful monovalent metal carbonates include lithium carbonate, cesium carbonate, rubidium carbonate, silver carbonate and cuprous carbonate. Examples of such a reaction are:

2c) $Na_2CO_3+2H_2O \rightarrow 2NaOH+CO_2+\frac{1}{2}O_2+H_2$; $E^0=1.52V$ and

2d) $K_2CO_3+2H_2O \rightarrow 2KOH+CO_2+\frac{1}{2}O_2+H_2$; $E^0=1.36V$

Another embodiment is an electrochemical cell in which the cathode has access to oxygen through an air cathode (or oxygen cathode) and water combines with oxygen gas to form hydroxyl ions. The cathode reaction in this instance is:

3a) $H_2O+\frac{1}{2}O_2+2e^- \rightarrow 2OH^-$, or $2M^++H_2O+\frac{1}{2}O_2+2e^- \rightarrow 2MOH$ (As in reaction 2a), above, the $M^+$ ion comes from the anode.)

The overall reaction is:

3b) $M_2CO_3+H_2O \rightarrow 2MOH+CO_2$

Examples of the overall reaction are:

3c) $Na_2CO_3+H_2O \rightarrow 2NaOH+CO_2$; $E^0=0.29V$

3d) $K_2CO_3+H_2O \rightarrow 2KOH+CO_2$; $E^0=0.13V$

Another embodiment of the invention is one in which the cathode contains a salt of a reducible metal ion. The cathode reaction is:

4a) $M'^{2+}+2e^- \rightarrow M'^0$; where $M'^{2+}$ is a reducible divalent metal ion, or 4b) $2M'^{2+}+2e^- \rightarrow 2M'^+$; where $M'^{2+}$ is a reducible divalent metal ion, or 4c) $2M''^{+}+2e^- \rightarrow 2M''^0$; where $M''^+$ is a reducible monovalent metal ion.

The overall reaction in general terms is:

4d) $M_2CO_3+M'A \rightarrow M_2A+CO_2+\frac{1}{2}O_2+M'^0$; where A is a divalent anion, or 4e) $M_2CO_3+M'A_2 \rightarrow 2MA+CO_2+\frac{1}{2}O_2+M'^0$; where A is a monovalent anion, or 4f) $M_2CO_3+2M'A \rightarrow M_2A+CO_2+\frac{1}{2}O_2+M'_2A$; where A is a divalent anion, or 4g) $M_2CO_3+2M'A_2 \rightarrow 2MA+CO_2+\frac{1}{2}O_2+2M'A$; where A is a monovalent anion, or 4h) $M_2CO_3+M''_2A \rightarrow M_2A+CO_2+\frac{1}{2}O_2+M'_2A$; where A is a divalent anion, or 4i) $M_2CO_3 3O 2M''A \rightarrow 2MA+CO_2+\frac{1}{2}O_2+2M''^0$; where A is a monovalent anion.

Examples of salts of reducible metal ions include silver sulfate, copper sulfate, and copper chloride. Generally, some water or other polar solvent is present as part of the anode and cathode. Examples of the overall reaction include:

4j) $Na_2CO_3+2AgCl \rightarrow 2NaCl+CO_2+\frac{1}{2}O_2+2Ag$; $E^0=0.47V$

4k) $Na_2CO_3+Ag_2SO_4 \rightarrow Na_2SO_4+CO_2+\frac{1}{2}O_2+2Ag$; $E^0=0.04V$ 4l) $Na_2CO_3+CuCl_2 \rightarrow 2NaCl+CO_2+\frac{1}{2}O_2+Cu$; $E^0=0.24V$ 4m) $Na_2CO_3+CuSO_4 \rightarrow Na_2SO_4+CO_2+\frac{1}{2}O_2+Cu$; $E^0=0.35V$ Other reducible mateddais useful as cathode components include halogen such as chlorine, bromine and, in particular, iodine which is solid at room temperature and Chalcogen, especially sulfur. Both iodine and sulfur are reducible and readily combine with a metal cation such as $Na^+$. The halogen cathode components may be combined with polymer materials such as poly-2-vinyl pydddene (P2VP) or carbon.

An example of the overall reaction with a halogen cathode is:

5) $Na_2CO_3+I_2 \rightarrow 2NaI+CO_2+\frac{1}{2}O_2$; $E^0=0.140V$

In general there are two benefits to utilizing the cathode reactions described in reactions 4a–4m and 5. For one, the absence of hydrogen evolution or oxygen consumption at the cathode enables the cell to be designed and constructed so that the cathode is sealed from the environment. This simplifies the design of the cell and provides the possibility of having the cell completely sealed except for an anode compartment gas vent opening, e.g., to a fluid reservoir. Such a design is conducive to implantable devices for medical purposes, for example. Secondly, the non-hydrogen releasing cathode reactions typically reduce the theoretical voltage required to drive the cell.

Under these scenarios, where the anode contains an electrolytically-decomposable metal carbonate, three molecules of gas are released at the anode per four electrons. Numerous electrolytes such as beta-alumina, beta"-alumina, NASICON (which is an acronym for "sodium super ion conductor"), or generally MESICON (which is an acronym for "metal ion super conductor), and solid polymer electrolytes may be considered to transport the metal ions from the anode to the cathode in the above identified reactions, especially 4a) through 4m). An example of solid polymer electrolyte is the copolymeric ion exchange material which is a fluorocarbon vinyl ether copolymer known generally as perfluorocarbon. A family of solid polymer electrolytes of this type is marketed by E. I. dupont under the name Nafion®.

It is preferable that the electrolyte be selective for cations over hydroxyl ions to prevent the transport of hydroxyl ions from the cathode to the anode. NASICON and MESICON solid electrolytes typically are selective to cations only and will not allow the transport of hydroxyl ions. Also, certain solid polymer electrolytes are laminated composites in which the layer facing the cathode has carboxylic acid functional groups whereby the transport of hydroxyl ions is inhibited. Such laminated solid polymer electrolytes are readily available from such manufacturers as E. I. Dupont and Asahi Glass.

In other embodiments of the invention, the anode contains an electrolytically-decomposable metal bicarbonate, wherein the metal ion is transportable through a properly-selected solid non-porous, i.e. impermeable, electrolyte and the carbonate forms oxygen and carbon dioxide gases.

The anode reaction is:

6) $2MHCO_3 \rightarrow 2M^++2CO_2+\frac{1}{2}O_2+H_2O+2e^-$; where $M^+$ is a monovalent metal ion.

For the cathode reaction there are several possibilities, each of which has an advantage. In one case, the cathode includes water which decomposes to hydrogen gas and hydroxyl ions.

The cathode reaction is:

7a) $2H_2O+2e^- \rightarrow H_2+2OH^-$, or $2M^++2H_2O+2e^- \rightarrow H_2+2MOH$ The overall reaction would be:

7b) $2MHCO_3+H_2O \rightarrow 2MOH+2CO_2+\frac{1}{2}O_2+H_2$

Examples of the bicarbonates include sodium bicarbonate and potassium bicarbonate. Examples of such a reaction are:

7c) $2NaHCO_3+H_2O \rightarrow 2NaOH+2CO_2+\frac{1}{2}O_2+H_2$; $E^0=1.62V$ and

7d) $2KHCO_3+H_2O \rightarrow 2KOH+2CO_2+\frac{1}{2}O_2+H_2$; $E^0=1.53V$

Another possibility is that the cathode has access to oxygen through an air cathode (or oxygen cathode) and water combines with oxygen gas to form hydroxyl ions. The cathode reaction is:

8a) $H_2O+\frac{1}{2}O_2+2e^- \rightarrow 2OH^-$, or $2M^++H_2O+\frac{1}{2}O_2+2e^- \rightarrow 2MOH$ The overall reaction is:

8b) $2MHCO_3 \rightarrow 2MOH+2CO_2$

Examples of the overall reaction are:

8c) $2NaHCO_3 \rightarrow 2NaOH+2CO_2$; $E^0=0.39V$

8d) $2KHCO_3 \rightarrow 2KOH+2CO_2$; $E^0=0.30V$

Another possibility is that the cathode may have a salt of a reducible metal ion. The cathode reaction is:

9a) $M'^{2+}+2e^-\rightarrow M'^0$; where $M'^{2+}$ is a reducible divalent metal ion, or 9b) $2M'^{2+}+2e^-\rightarrow 2M'^+$; where $M'^{2+}$ is a reducible divalent metal ion, or 9c) $2M''^++2e^-\rightarrow 2M''^0$; where $M''^+$ is a reducible monovalent metal ion.

The overall reaction would be:

9d) $2MHCO_3+M'A\rightarrow M_2A+2CO_2+\frac{1}{2}O_2+M'^0+H_2O$; where A is a divalent anion, or 9e) $2MHCO_3+M'A_2\rightarrow 2MA+2CO_2+\frac{1}{2}O_2+M'^0+H_2O$; where A is a monovalent anion, or 9f) $2MHCO_3+2M'A\rightarrow M_2A+2CO_2+\frac{1}{2}O_2+M'_2A+H_2O$; where A is a divalent anion, or 9g) $2MHCO_3+2M'A_2\rightarrow 2MA+2CO_2+\frac{1}{2}O_2+2M'A+H_2O$; where A is a monovalent anion, or 9h) $2MHCO_3+M''_2A\rightarrow M_2A+2CO_2+\frac{1}{2}O_2+M'_2A+H_2O$; where A is a divalent anion, or 9i) $2MHCO_3+2M''A\rightarrow 2MA+2CO_2+\frac{1}{2}O_2+2M''^0H_2O$; where A is a monovalent anion.

Examples of salts of reducible metal ions include silver sulfate, copper sulfate, and copper chloride. Examples of the overall reaction include:

9j) $2NaHCO_3+2AgCl\rightarrow 2NaCl+2CO_2+\frac{1}{2}O_2+2Ag+H_2O$; $E^0$=0.57V 9k) $2NaHCO_3+Ag_2SO_4\rightarrow Na_2SO_4+2CO_2+\frac{1}{2}O_2+2Ag+H_2O$; $E^0$=0.14V 9l) $2NaHCO_3+CuCl_2\rightarrow 2NaCl+2CO_2+\frac{1}{2}O_2+Cu+H_2O$; $E^0$=0.34V 9m) $2NaHCO_3+CuSO_4\rightarrow Na_2SO_4+2CO_2+\frac{1}{2}O_2+Cu+H_2O$; $E^0$=0.45V Generally, in the above reactions involving bicarbonates, as well as those involving carbonates, it is desirable that the cathode and anode mateddais be at least partially in solution, i.e., a polar solvent such as water, is present. An advantage of the use of carbonates or bicarbonates to generate gas is that they generally have relatively high water solubility and are ionic compounds. That is, the bonding between the metal and carbonate or bicarbonate portions of the compound is ionic. Thus, addition of other ionic materials such as NaOH or KOH is unnecessary to the formation of an electrolytic composition. Thus, all the materials present, e.g. carbonate/bicarbonate/water decompose to produce gas. The metal portion useful carbonates and, in particular, bicarbonates may include sodium, potassium, lithium, rubidium, cesium, silver, copper and mixtures thereof.

Other reducible materials useful as cathode components include halogen such as chlorine, biomine and, in particular, iodine which is solid at room temperature and chalcogen, especially sulfur. Both iodine and sulfur are reducible and readily combine with a metal cation such as $Na^+$. The halogen cathode components may be combined with polymer materials such as poly-2-vinyl pyridene (P2VP) or carbon.

An example of the overall reaction with a halogen cathode is:

10) $2NaHCO_3+I_2\rightarrow 2NaI+CO_2+H_2O+\frac{1}{2}O_2$; $E^0$=0.54V

Again, in general there are two benefits to utilizing the cathode reactions described in reactions 9a–9m & 10. For one, the absence of hydrogen evolution or oxygen consumption at the cathode enables the cell to be designed and constructed so that the cathode is sealed from the environment. This simplifies the design of the cell and provides the possibility of having the cell completely sealed except for an anode compartment gas vent opening, e.g., to a fluid reservoir. Such a design is conducive to implantable devices for medical or other purposes. Secondly, the non-hydrogen releasing cathode reactions typically reduce the theoretical voltage required to drive the cell.

Under these scenarios, where the anode contains an electrolytically-decomposable metal bicarbonate, five molecules of gas are released at the anode per four electrons. Numerous electrolytes such as beta-alumina, beta"-alumina, NASICON, or generally MESICON, and solid polymer electrolyte such as Nation® may be utilized to transport the metal ions from the anode to the cathode. NASICON is further described in "Compositions for Fast Alkali-Metal-Ion Transport," U.S. Pat. No. 4,049,891, issued Sep. 20, 1977 and *Solid State Chemistry of Energy Conversion and Storage, Advances in Chemistry Series No. 163*, H. Y-P. Hong, ed. J. B. Goodenough and M. S. Whittingham, ACS pub., (1977), p. 179 which are incorporated herein.

The term "MESICON" embraces NASICON ceramics and may be represented by the formula $Me_5ReSi_4O_{12}$ wherein Me is a metal selected from the class consisting of potassium, sodium, lithium, silver and Re is a rare earth metal or yttrium.

Various composition formulas have been described for metal super ion-conductors. For example, there are Nasicon-type materials having various formulas, including $Na_{1+x}Zr_xP_{3-x}Si_xO_{12}$ where zero $\leq x \leq$ three and $Na_3M_2(PO_4)_3$ where M=Sc, Cr or Fe. There are also so-called "LISICON" materials, such as $LiZr_2(PO_4)_3$ and $Li_3Zr_2Si_2PO_{12}$. And other material formulations include $Me_3Zr_2Si_2PO_{12}$, where Me-Na, Li, Ag or K; $Me_5GdSi_4O_{12}$ where Me=Ag, Li or Na; and $A_xTi_3P_6Si_2O_{25}$ where A=Li, Na and K, and $0\leq x \leq 2$.

As with the electrolytes suitable for the carbonate decomposition, it is preferable that the electrolyte be selective for cations over hydroxyl ions to prevent the transport of hydroxyl ions from the cathode to the anode. In addition, it is preferable that the cationic electrolyte separator be selective to the metal ion of the bicarbonate over the proton. If the proton is conducted in addition to the metal ion, then the amount of gas generated for a given amount of current passing through the cell circuit will approach only three molecules of gas per four electrons as is the case for the reactions 4a–4m and 5 above. NASICON and MESICON solid electrolytes typically are selective to cations only and will not allow the transport of hydroxyl ions. Rare earth element NASICON is also the subject of H. Y-P. Hong, J. A. Kafalas, and M. Bayard, *Material Research Bull.*, Vol. 12 (1978), pp. 969–973; R. D. Shannon, H-Y. Chen, and T. Berzins, *Material Research Bull.*, Vol. 12, (1977), pp. 969–973; R. D. Shannon, B. E. Taylor, T. E. Gier, H-Y. Chen, and T. Berzins, *Inorganic Chemistry*, Vol. 17 [4], (1978), pp. 958–964; and B. A. Maximov, I. V. Petrov, A. Rabenau, and H. Schultz, *Solid State Ionics*, Vol. 6, (1982), pp. 195–200 which are included herein.

Cation-conducting ceramics, such as beta-aluminas, NASICON and MESICON, may be made to transport a large variety of metal cations, including divalent as well as monovalent ions. For the purposes of this invention, cation-conducting ceramics are those having a mobile monovalent metal ion in the structure selected from the group consisting of sodium, potassium, lithium, rubidium, cesium, silver and copper (valence +1).

Composite polymeric electrolytes containing ion conducting ceramic providers such as those described in Lee et al., U.S. Pat. No. 4,990,413 are also useful as ion transporting separates in the instant invention.

Another type of coulombically efficient gas generating cell which releases more than one molecule of non-combustible gas per four electrons is one where the cathode contains a reducible metal carbonate or basic carbonate and an oxygen evolution electrode is placed opposite with a bicarbonate ion permeable separator placed therebetween. The anode reaction is the following:

11a) $CO_3^{-2} \rightarrow \frac{1}{2}O_2 + CO_2 + 2e^-$ and/or;

11b) $2HCO_3^- \rightarrow \frac{1}{2}O_2 + 2CO_2 + H_2O + 2e^-$ and/or;

11c) $2OH^- \rightarrow \frac{1}{2}O_2 + H_2O + 2e^-$

At the cathode, a metal carbonate or basic metal carbonate is reduced:

12a) $M'CO_3 + 2e^- \rightarrow M'^0 + CO_3^{-2}$, or

12b) $M'CO_3 \cdot M'(OH)_2 + H_2O + 4e^- \rightarrow 2M'^0 + HCO_3^- + 3OH^-$; or 12c) $M'CO_3 \cdot M'(OH)_2 + 4e^- \rightarrow 2M'^0 + CO_3^{-2} + 2OH^-$; or 12d) $2M'CO_3 \cdot M'(OH)_2 + 2H_2O + 6e^- \rightarrow 3M'^0 + 2HCO_3^- + 4OH^-$; or 12e) $2M'CO_3 \cdot M'(OH)_2 + 6e^- \rightarrow 3M'^0 + 2CO_3^{-2} + 2OH^-$;

Overall reactions would be:

13a) $M'CO_3 + 2e^- \rightarrow M'^0 + CO_2 + \frac{1}{2}O_2$

13b) $M'CO_3 \cdot M'(OH)_2 \rightarrow 2M'^0 + CO_2 + O_2 + H_2O$

13c) $2M'CO_3 \cdot M'(OH)_2 \rightarrow 3M'^0 + 2CO_2 + \frac{3}{2}O_2 + H_2O$

Examples of the carbonates in cathode reactions 12a–e could be $NiCO_3$, $CuCO_3 \cdot Cu(OH)_2$ (malachite), or $2CuCO_3 \cdot Cu(OH)_2$ (azurite). Generally, water is also present in the cathode as well as a metal hydroxide or carbonate to enhance the conductivity of the cathode.

Carbon dioxide gas released at the cathode may either permeate through the cathode and separator to join the oxygen which is released at the anode, or the carbon dioxide may flow directly from the cathode to join the anode gas.

In all of these cases described hereinabove, non-combustible, non-toxic gas mixtures of oxygen and carbon dioxide are produced electrochemically. The addition of carbon dioxide to the mixture enables dispensing a greater volume of fluid for a given amount of electrical current when the gas generation cell is coupled to a fluid dispensing device.

In some applications, it may be preferable to generate, at a steady rate, carbon dioxide without any oxygen. For example, fluids which are particularly sensitive to oxidation may preferably be dispensed utilizing a gas generator producing only carbon dioxide as the pressurizing gas. For such purposes, the instant invention may be coupled with an oxygen absorbent. The patent literature describes several alternatives of achieving this purpose.

Examples of oxygen absorbents are disclosed in U.S. Pat. Nos. 4,104,192 and 4,113,652 and 4,192,773 by Yoshikawa et. al., U.S. Pat. No. 4,199,472 by Ohtsuka et. al., U.S. Pat. No. 4,166,807 by Komatsu et. al. and U.S. Pat. No. 4,127,503 which are incorporated herein. Oxygen absorbents include reducing agents, such as iron powder, oxalates, sulfites, hydrogen sulfites, dithionites, pyrogallol, Rongalit, glucose, copper amine complex, zinc powder and the like, and any compositions containing a suitable reducing agent. The absorbent could be a solid oxygen absorbent or a solid carder impregnated with a liquid oxygen absorbent.

In the cases above, as oxygen is absorbed from the anode gas stream, the amount of gas available for driving a fluid delivery system is reduced by one molecule per four electrons; however, Takahashi et al. in U.S. Pat. No. 4,524,015, incorporated herein, discloses an oxygen absorbent system which releases carbon dioxide stoichiometrically as oxygen is absorbed, thus the resulting gas stream is composed of only carbon dioxide which has flow rate proportional to the cell current, and which is coulombically-efficiently generated. In such a system, a particulate or granular oxygen absorbent comprising at least one ascorbic compound selected from ascorbic acid, ascorbic acid salt or mixtures thereof, an alkali metal carbonate, an iron compound, carbon black and water is utilized.

The coulombically efficient electrochemical gas generator of this disclosure delivers gas at substantially constant rates when coupled with a battery or batteries in series or parallel. Rates can be adjusted through the addition of a resistor in the circuit external to the cell. Flow rate can be increased by decreasing the resistance of the resistor or conversely the rate can be decreased by increasing the level of resistance. Utilizing a controller to adjust the resistance of the resistor to control the flow rate is within the scope of this invention. Alternately, an adjustable DC power supply coupled to a controller may be utilized instead of the battery or batteries and resistor. The controllers may have a manual interface so that an operator may select the desired gas generation flow rate, or the controller may be coupled with a sensor or bio-feedback sensor so that the flow rate is adjusted in response to a changing demand.

DETAILED DESCRIPTION OF INVENTION

Figure 1:
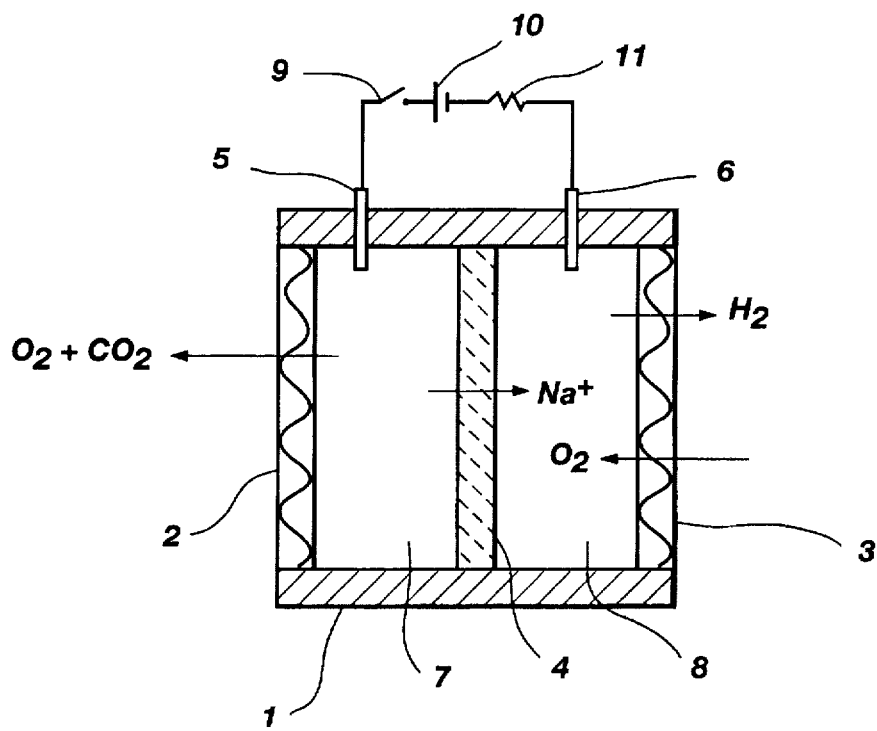
FIG. 1 is a schematic representation of an electrochemical cell embodying the instant invention.

Detailed description of the instant invention may be facilitated by reference to FIG. 1 which is a schematic of a cell having corrosion resistant container 1, an anode 7, a cathode 8, with a cation conducting separator 4, e.g., beta alumina, therebetween. Anode current collector and contact 5 is in electrical communication with the anode and an external circuit which may include a switch 9, a DC power source such as a battery 10, optionally a resistor 11, and a cathode current collector and contact 6 which is in electrical communication with the cathode.

The anode material is bounded by the container or housing 1, the separator 4, and a hydrophobic gas permeable diffusion barrier 2. The anode gas diffusion barrier 2 is permeable to oxygen and carbon dioxide gases which diffuse out of the cell, but the barrier prevents electrolyte in the anode from flowing out of the cell. Likewise, the cathode gas diffusion barrier 3 is permeable to oxygen which diffuses into the cathode or hydrogen gas which diffuses out of the cathode depending on how the cell is to be operated, but the barrier prevents electrolyte in the cathode from flowing out of the cell.

In some embodiments of the invention, as stated hereinabove, the cathode compartment is completely sealed from the external environment. As electrons flow through said circuit, oxygen and carbon dioxide are generated and released at the anode when the cell contains a carbonate or bicarbonate compound as described hereinabove. The separator 4 is a solid impermeable ceramic electrolyte when a cation, e.g. $Na^+$, is to be transported from the anode to cathode, and is a permeable, hydroxyl ion, bicarbonate ion or carbonate ion transporter when such ions are to be transported from the cathode to anode.

Such a cell would be suitable for electrochemically decomposing a metal carbonate or metal bicarbonate at a rate directly proportional to the current according to reactions 2b–2d, 3b–3d, 7b–7d, or 8b–8d above. The carbonate or bicarbonate would be a constituent of the anode along with water. In addition, the anode may advantageously contain an electronic conductor such as finely divided graphite or a finely divided metal powder which oxidizes at a higher potential than the carbonate. The anode preferably also includes an electrocatalyst which promotes the evolution of oxygen. Finely divided platinum black powder, precious metal oxide such as ruthenium and/or iridium oxide, or ruthenium and or iridium metal, or nickel oxide, or nickel or other suitable electrocatalyst are useful.

The cathode may contain water, preferably with some initial metal hydroxide or metal carbonate to reduce the resistance of the electrode. The cathode may also contain an electronic conductor such as finely divided graphite or a finely divided metal powder. If the cathode is to be operated such that hydrogen gas is evolved, then a suitable electrocatalyst should be incorporated into the cathode. Such a suitable cathode electrocatalyst for hydrogen evolution would be Raney nickel.

If the cathode is to be operated such that oxygen is reduced, then a suitable electrocatalyst should be incorporated into the cathode. Such suitable cathode electrocatalysts for oxygen reduction would include platinum, platinum reduced onto carbon, tungsten oxide ($W_{18}O_{49}$), or the perovskite $La_xWO_3$, where $0.1<x<1$. The latter two electrocatalysts are particularly suited for alkaline conditions according to Kohler and Göpel in "Catalysis of the Oxygen Reduction on $W_{18}O_{49}$ Electrodes by $OH^-$ Induced Surfaces States," J. Electrochemical Soc., Vol. 139, No. 11, pp. 3035–3042, incorporated herein by reference.

Both anode and cathode may include gelling agents to reduce the likelihood of leakage. Suitable gelling agents include modified starches and cellulose materials, e.g., carboxymethyl cellulose, such as Waterlock or Carbopol or poly vinyl alcohol (PVA).

When the anode contains a metal carbonate, numerous separators such as beta-alumina, beta"-alumina, NASICON or generally MESICON and solid polymer electrolytes may be utilized to transport metal ions from the anode to the cathode. Preferred separators are characterized by having very low electronic conductivity relative to ionic conductivity. It is preferable that the separator be selective for cations over hydroxyl ions to prevent the transport of hydroxyl ions from the cathode to the anode when a metal carbonate is present as part of the anode. NASICON and MESICON electrolytes typically are selective to cations only and will not allow the transport of hydroxyl ions. Also, certain solid polymer electrolytes are laminated composites in which the layer facing the cathode has carboxylic acid functional groups where the transport of hydroxyl ions is inhibited. Such laminated solid polymer electrolytes are readily available from such manufacturers as E. I. Dupont and Asahi Glass under the names Nafion® and Flemion® respectively.

When the anode contains a metal bicarbonate, it is preferable that the cationic electrolyte separator be selective to the metal ion of the bicarbonate over the proton. If protons are conducted in addition to the metal ion, then the amount of gas generated for a given amount of current passing through the cell circuit will approach only three molecules of gas per four electrons as is the case for the reactions 4a–4m above. NASICON and MESICON electrolytes typically are selective to cations only and will not allow the transport of hydroxyl ions. Certain rare earth element NASICON's disclosed in Balagopal et. al.'s U.S. patent application Ser. No. 08/204,026 are particularly suited for this application since they are highly selective toward non-protonic cation conduction at relatively low resistances and at ambient temperatures.

Figure 2:
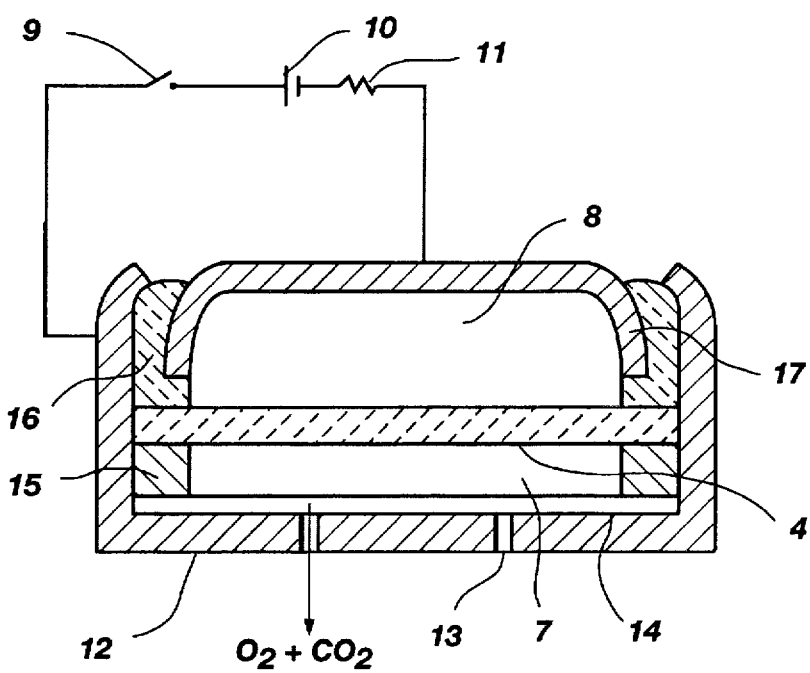
FIG. 2 is a sectional view of an electrochemical cell which produces oxygen and $CO_2$ at the anode without any production or consumption of gas at the cathode.

FIG. 2 shows a sectional view of a gas generating cell where neither hydrogen is generated at the cathode nor is oxygen consumed, and where both oxygen and carbon dioxide are released at the anode. The cell is constructed similar to a button cell battery. A metallic, electronically conductive can (housing) 12 is crimped over an electronically insulating grommet 16, and metallic, electronically conductive cap 17. The can has one or more perforations 13 in the wall of the anode compartment which allow anode gases to exit the cell. A hydrophobic but gas permeable film 14 comprised of polyolefin, fluoropolymer, or other suitable material is positioned on the inner flat surface of the can (housing) to retain liquid in the anode but allow the product gases to exit through the perforation(s). The metal ion conductive separator 4 is supported by the grommet 16 on the cathode side and by an electronically conductive gasket 15 on the anode side. The gasket may be comprised of carbon or metallic fibers or electronically conductive elastomers.

The anode and separator have the same features and functions as those described for FIG. 1. The anode contains a decomposable metal carbonate and the cathode 8 contains a reducible metal salt such as copper chloride, copper surfate, or silver sulfate. As current passes through the circuit, oxygen and carbon dioxide are released at the anode, metal ions migrate under a potential gradient through the separator, e.g. NASICON, to form metal salt in the cathode as metal is reduced at the cathode according to reactions 4d–4m and 9d–9m described above. Constituents of the anode are the same as that for the anode described in FIG. 1. Besides a reducible metal salt, the cathode may include water, and may include an electronically conductive material such as finely divided graphite, carbon, or metal. Both anode and cathode may include gelling agents to reduce the likelihood of leakage. Suitable gelling agents include modified starches and cellulose materials such as Watefiock or Carbopol. The grommet 16 serves three purposes, it electrically isolates the cap 17 (which is in electrical communication with the cathode 8) from the can 12 (which is in communication with the anode 7). The grommet also seals the cathode materials from the environment and seals the cathode materials from the anode materials by sealing against the separator. The grommet is of a non-electronic conducting material and has suitable resilience and impermeability to conform to the shape of the container to act as a seal.

Figure 3:
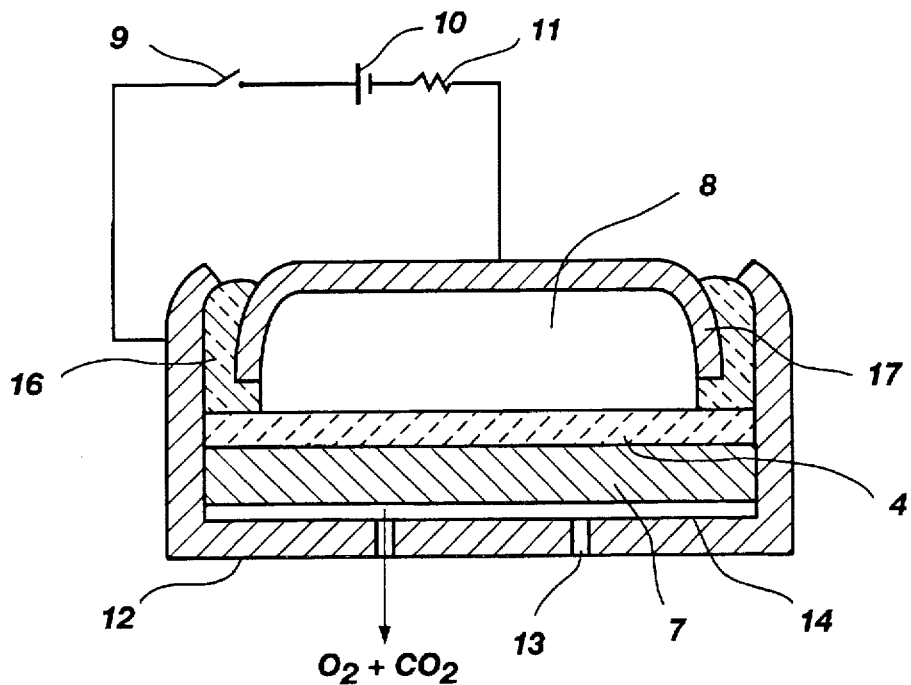
FIG. 3 is an illustration of a cell structurally similar to the cell for FIG. 2 without an electronically conductive gasket.

FIG. 3 shows a variation of the gas generation cell shown in FIG. 2. In this variation, the electronically conductive gasket 15 is eliminated and the anode 7 is consolidated into an electronically conductive matrix which serves as a current collector and support for the separator 4.

Figure 4:
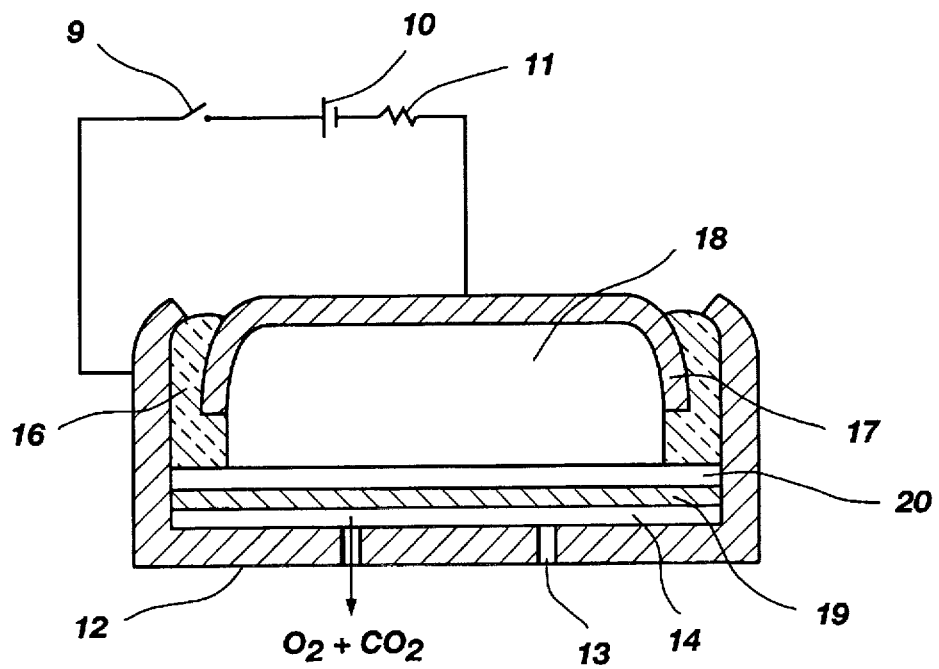
FIG. 4 is an illustration of a cell structurally similar to the cell of FIG. 3 in which a different separator is utilized and a different cathode composition is present.

The electrochemical gas-generating cell shown in FIG. 4 has substantially the same components used as the cell shown in FIG. 3; however, there are some fundamental differences such at the type of separator utilized and location of a decomposable carbonate. The active constituent of the cathode 18 is a reducible metal carbonate or reducible basic metal carbonate such as $NiCO_3$, $CuCO_3 \cdot Cu(OH)_2$ (malachite), or $2CUCO_3 \cdot Cu(OH)_2$ (azurite). The cathode also contains an aqueous metal hydroxide or carbonate such as sodium or potassium hydroxide or carbonate and may include an electronically conductive material such as finely divided graphite, carbon, or metal. Also, electrocatalysts may be included, if desired. In addition, the cathode may include gelling agents to reduce the likelihood of leakage. Suitable gelling agents include modified starches and cellulose materials such as Watedock or Carbopol or poly vinyl alcohol. The anode primarily consists of an electronically-conductive material with a catalyst suitable for oxygen evolution in an basic environment. According to Corrigan in "The Catalysis of the Oxygen Evolution Reaction by Iron Impurities in Thin Fihn Nickel Oxide Electrodes," J. Electrochemical Soc., Vol. 134, No. 2. pp. 377–384, suitable electrocatalysts are nickel oxide or nickel/iron oxide, nickel and nickel plated steel. The anode materials may also have an amount of hydrophobic material such as fine Teflon powder added to reduce flooding of the electrode. The construction of the anode may be very similar to the construction of the air cathode of the zinc/air battery or gas diffusion electrodes of solid-polymer, electrolyte fuel cells. The difference is that a catalyst suitable for oxygen evolution in basic (alkaline) solution is utilized.

Unlike the cells described in FIGS. 1-3, this cell utilizes a separator 20 which is permeable preferably to hydroxyl ions, carbonate ions or bicarbonate ions There are numerous suitable separators available, many of which are utilized by the alkaline cell battery industry. Several microporous separators are readily available. Many have wetting agents on the surfaces which allow water and hydroxyl ions to migrate or diffuse through more easily, such separators are produced by Pall RAI, and by Hoechst Celanese. Another suitable separator consists of a nonwoven polypropylene filter media impregnated with a 5–10% solution of polyvinyl alcohol. The overall cell reactions are 13a–13c described above.

Another variation of this type of cell is one where the anode gas diffusion barrier 2 is omitted and where the bottom inner surface of the can 12 serves as the anode. The diffusion barrier becomes optional if the cell is integrated to a fluid dispensing reservoir as shown in FIG. 6; however, the barrier is still desirable to contain the electrolyte, thereby maintaining good ionic conductivity.

Figure 5:
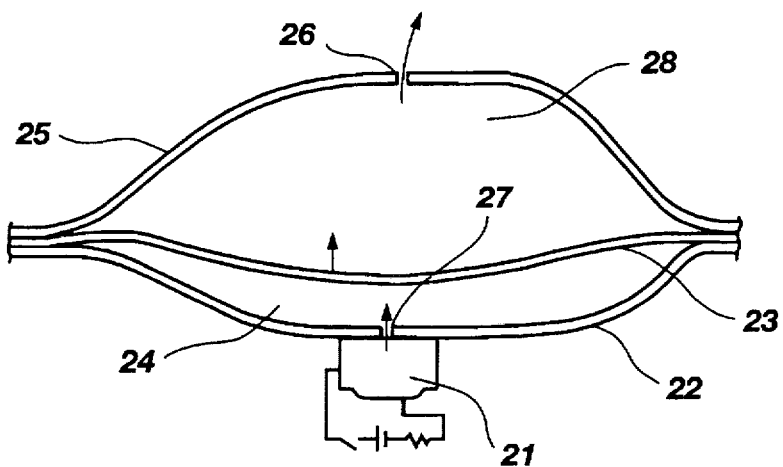
FIG. 5 is a schematic illustration of an electrochemical cell of the instant invention coupled to a fluid dispensing reservoir.

FIG. 5 shows schematically how an electrochemical gas generating cell 21 of the instant invention could be coupled to a fluid dispensing reservoir. The reservoir consists of an upper shell 25, a lower shell 22 and a flexible diaphragm 23. The gas-generating cell electrochemically releases oxygen and carbon dioxide gas into the pressurizing chamber 24 through opening 27. As gas enters the chamber, pressure rises in fluid chamber 28 where the fluid intended to be dispensed is stored. As the pressure rises in the fluid chamber, fluid exits through port 26 at a rate directly proportional to the rate at which gas enters the pressurizing chamber, which is also directly proportional to the electrical current passing through the cell circuit.

Figure 6:
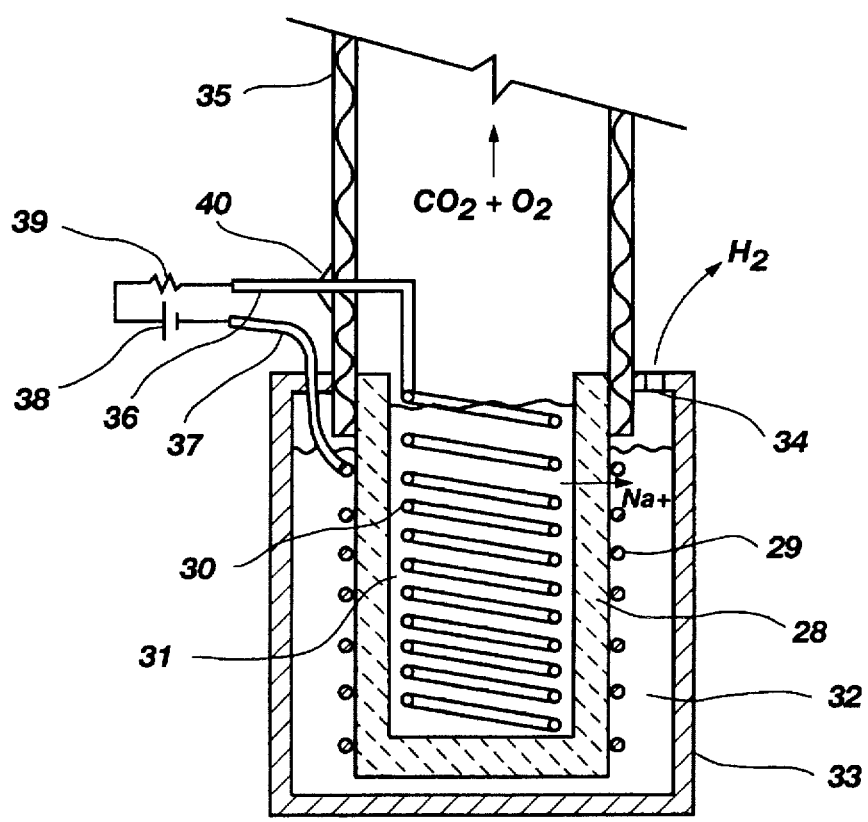
FIG. 6 is a schematic illustration of a gas generating electrochemical cell utilizing a cylindrical ceramic transport member.

FIG. 6 shows schematically a variation of a gas-generating cell wherein a cylindrical ceramic metal ion conducting separator (solid electrolyte) 28 is utilized to separate the anode from the cathode. The cathode 32 is contained between the outer shell 33 and said cylindrical separator. In this embodiment, a cathodic current collector coil 29, such as a nickel wire coil, is shown, which is connected to or becomes cathodic lead 37, which passes through said outer shell to be connected to an external circuit. In the compartment formed by the cylindrical separator 28 is the anode 31. In this embodiment, an anodic current collector coil 30 such as nickel wire coil is shown which is connected to the external circuit. An anode gas composition consisting of oxygen and carbon dioxide is released from the anode as current passes through the circuit. These gases flow through tubing 35 which leads to one chamber of a two-chamber, fluid reservoir with flexible diaphragm (not shown). Such a two-chamber reservoir may be similar to the one illustrated in FIG. 5.

Such a device is very simple in construction. Depending on the cathode material and operating voltage, a cathode gas port 34 is required to allow oxygen in or allow hydrogen gas to be vented, depending upon the type of materials in the cathode, as illustrated in the reactions identified hereinabove. Alternately, port 34 may be omitted if a salt of a reducible metal ion is utilized in the cathode or if a reducible halogen is utilized. The cathode 32 may or may not include an electronically-conductive component such as graphite, carbon, or freely divided metal and may or may not include a gelling agent. An electrocatalyst, if desired, may be included.

The anode 31 must include either a metal carbonate or bicarbonate. In addition, the anode may or may not include an electronically conductive component such as graphite, carbon, or finely divided metal and it may or may not include a gelling agent. Also, an electrocatalyst may be included.

The outer shell preferably is impervious to water and is chemically compatible with the cathode. If a cathodic current collector 29 is utilized, then the outer shell may be an electronic insulator such as polypropylene, polyvinyl chloride, or the like. If the outer shell is an electronic conductive material such a nickel, then the current collector can be omitted and the cathodic lead 37 may be connected directly to the outer shell. In the embodiment shown in FIG. 6, the tubing 35 is a flexible plastic material such as low density polyethylene which has reasonably low oxygen and carbon dioxide permeability and forms a seal where connected to the cylindrical separator. A sealant 40 is applied where the anodic lead passes through the tubing. Alternatively, rigid tubing may be utilized and sealant applied to the joint between the separator and the tubing. Another alternative embodiment is one in which the tubing is an electronic conductive material which has an outer diameter nearly the same as the inner diameter of the cylindrical separator. The tubing makes contact with an electronically conductive anode material or with the anodic current collector. The anodic lead is then connected to the outside of the conductive tube.

Figure 7:
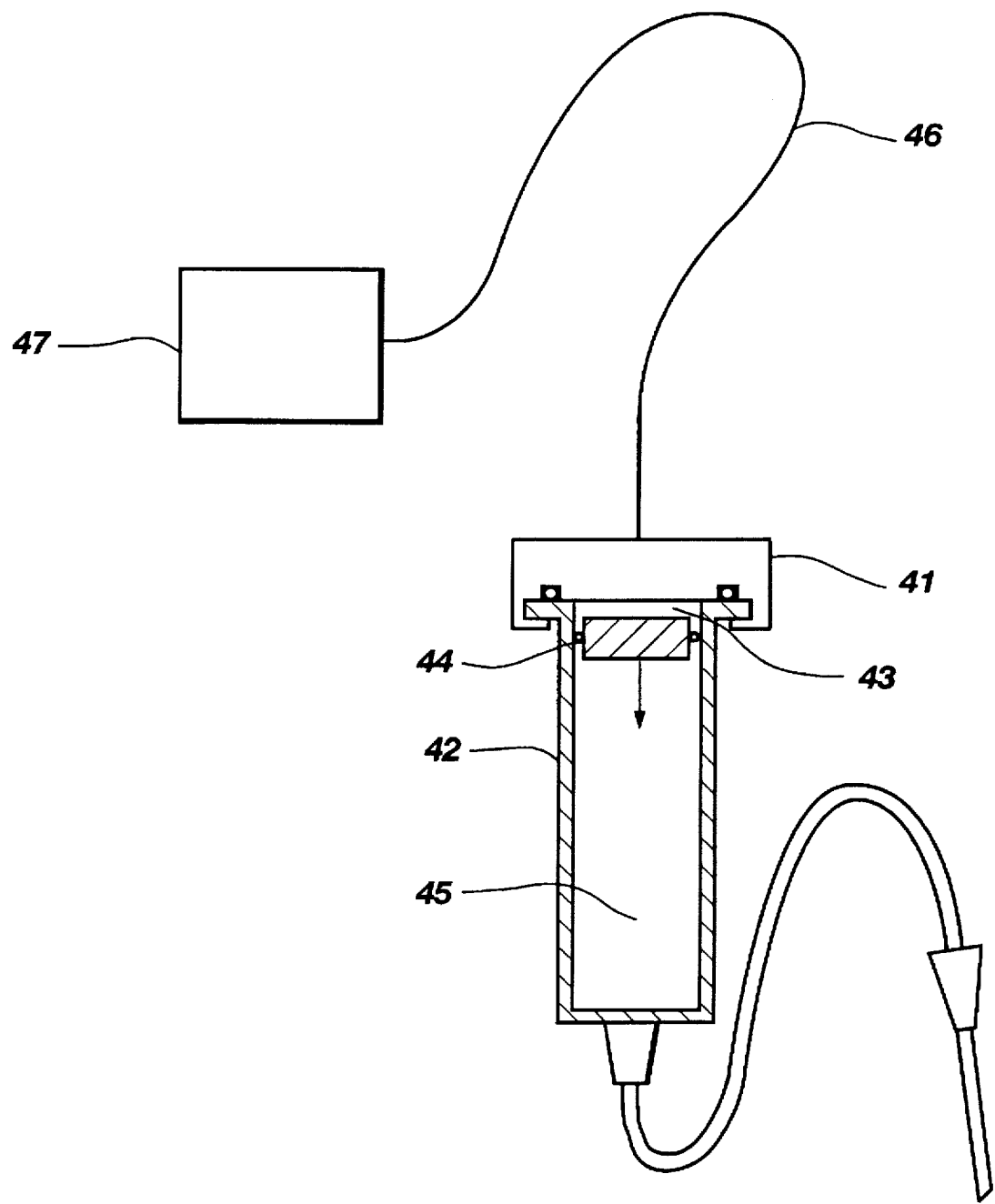
FIG. 7 is a schematic illustration of a gas generating electrochemical cell coupled to a syringe.

FIG. 7 shows a schematic of the coulombically-efficient electrochemical gas generator of the present invention 41 coupled with a syringe 42. Instead of the generated gas displacing a flexible diaphragm, the gas, discharged into chamber 43 propels the movement of a plunger 44 which in turn dispenses a fluid 45. In this embodiment, the electrochemical cell is connected through twisted pair leads 46 to a remote controller 47. The fluid may be a medication, the syringe may be fastened to the arm of an ambulatory recipient of the medication, and the controller may be worn at a convenient location such as at the waist. Batteries in the controller may also be utilized to drive the gas generator. The controller may also optionally receive feedback from the recipient of the medication through the use of a sensor.

Figure 8:
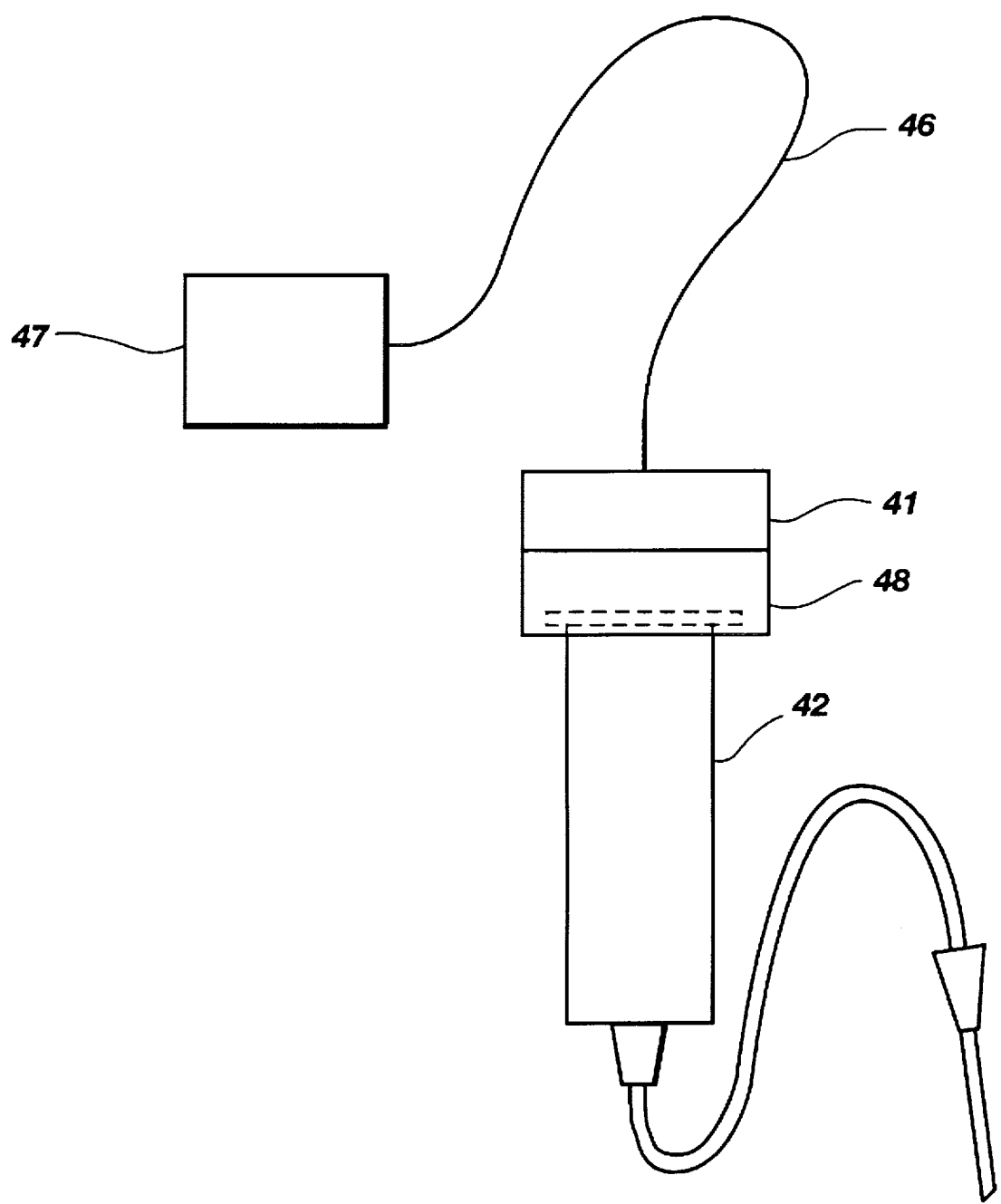
FIG. 8 is a schematic illustration of a gas generating cell having an oxygen absorber interposed between the cell and a fluid delivery device.

FIG. 8 shows a schematic of the coulombically-efficient electrochemical gas generator of the present invention 41 coupled with a syringe 42, where an oxygen absorber 48 has been placed in the gas flow line to absorb oxygen so that only carbon dioxide flows to the syringe.

Figure 9:
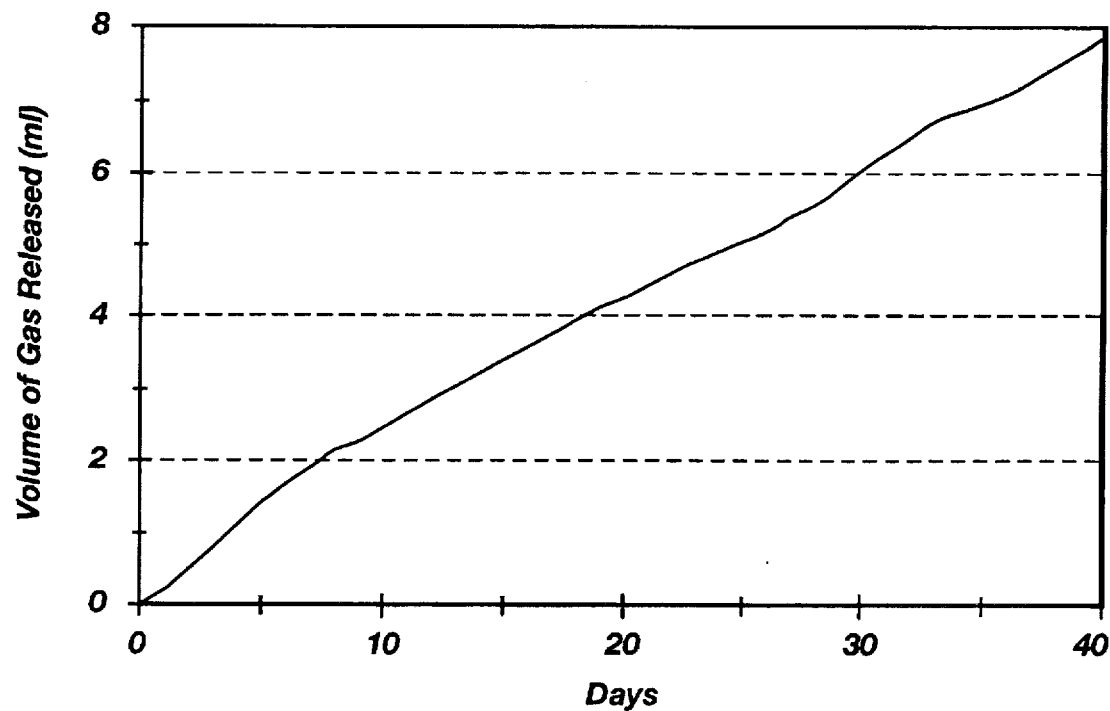
FIG. 9 is a graph illustrating fluid dispensed over various time periods for a fluid dispensing device using a particular gas generating cell of the instant invention.

FIG. 9 shows a plot of water dispensed versus time using a reservoir like the one shown in FIG. 5 and an electrochemical gas-generating cell like the one shown in FIG. 4 where the anode gas diffusion barrier 2 was omitted and the nickel plated steel can 12 served as the anode. The anion transporting separator was made by Pall RAI company, Hauppauge, N.Y., and the cathode consisted of 55% $CuCO_3 \cdot Cu(OH)_2$ (malachite) and 45% 7.5N KOH. The cell was driven by a DC power supply at a voltage typical of a silver oxide battery. The circuit included a 8200-$\Omega$ resistor. The rate of water dispensed was substantially linear with respect to time over an extended period without an elaborate means of controlling the rate other than the initial selection of a resistor. The diameter of the can was approximately 0.5 inch. There were three 0.020 inch diameter perforated holes in the can adjacent the anode to allow the gas to enter the pressurizing chamber. No vents were provided adjacent the cathode.

Figure 10:
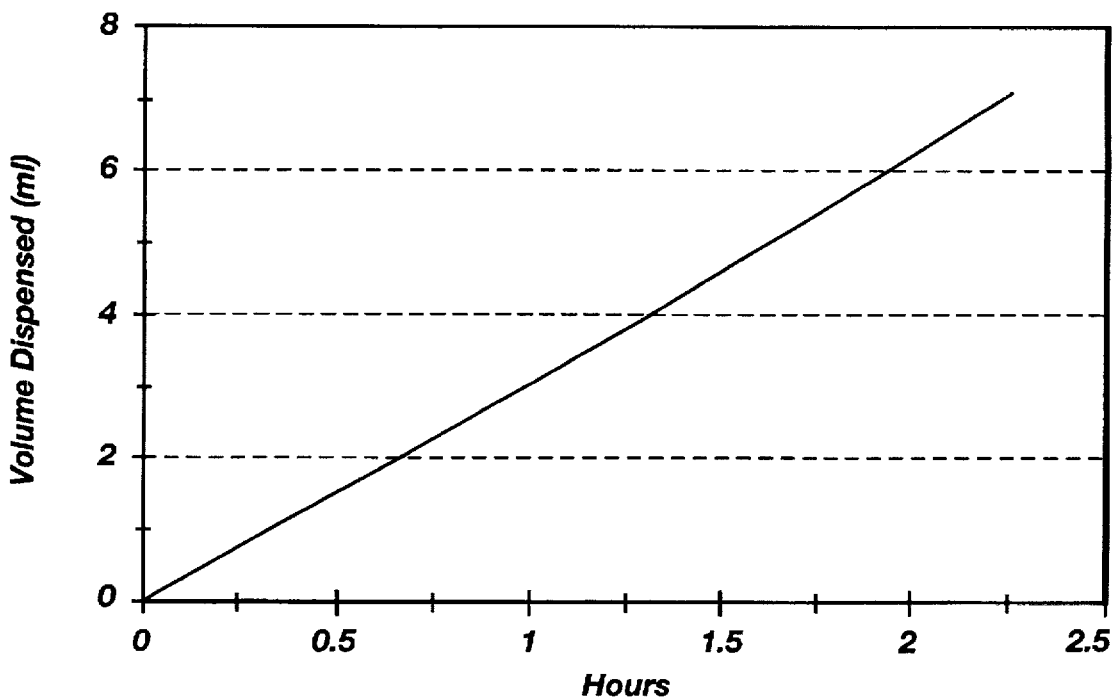
FIG. 10 is a graph illustrating gas volume generated over various time periods for a cell similar to that illustrated in FIG. 6.

FIG. 10 shows a plot of gas volume generated versus time using an embodiment of the device similar to what is shown in FIG. 6. The cylindrical separator was constructed of the sodium conducting ceramic, NASICON with a composition of $Na_3ZrSi_2PO_{12}$. The material was produced using solid state processing, a technique which is well known in the art and which is described elsewhere, J. Alamo and R. Roy, "Ultralow Expansion Ceramics in the System $Na_2O$-$ZrO_2$-$P_2O_5$-$SiO_2$." J. Am. Ceram. Soc., 67 [5] C-78-C-79 (1984). Precursor powder materials of $Na_2CO_3$, $ZrO_2$, $SiO_2$, and $Zr_2PO_4$ were mixed in the appropriate ratios and then calcined to form a $Na_3ZrSi_2PO_{12}$ material which was milled into fine powder. Cylinders with a single closed end were pressed from the powder using a die. These parts were then sintered, resulting in parts with no through porosity. The final ceramic part had an inner diameter of 1 centimeter with 3.5 cm height. Nickel wire was used for the anodic and cathodic current collectors. The outer container was constructed of glass. The anode consisted of a slurry of 70% $NaHCO_3$ and 30% water. The cathode was a solution of 3% NaOH. Approximately 10 square centimeters of the separator were active. Tygon™ flexible plastic tubing was connected to the gas-generating device at one end and a displacement-type, gas-volume, measuring device at the other end. The gas-generating device was connected to a circuit including a power supply at 1.7V and a 100 ohm resistor. The plot of gas volume dispensed versus time is substantially linear with respect to time. A comparison of current integrated with time versus the volume of gas generated indicated that approximately 4.5 molecules of gas were collected per four electrons passed. Thus the device was coulombically efficient with respect to other devices known in the art.

Although several embodiments of the invention have been shown and described, it will be obvious that other adaptations and modifications can be made without departing from the true spirit and scope of the invention.

What is claimed is:

1. A device for electrochemically generating carbon dioxide gas or a mixture of carbon dioxide and oxygen gases in an adjustable quantity proportional to the cell current, comprising:

an electrochemical cell having a corrosion resistant container or housing;

a cathode chamber containing an electronically conductive current collector and adapted to contain a reducible material;

an anode chamber containing an electronically conductive current collector and adapted to contain an oxidizable material wherein said oxidizable material is a metal carbonate, metal bicarbonate, or combination thereof, and wherein the anode chamber structure has perforations or diffusion pores to permit gas to be released;

an ionically conductive separator between the anode chamber and cathode chamber structured to maintain physical separation of the materials in each chamber; and optionally a switch and variable or fixed resistor forming a circuit with said power source and electrochemical cell.

2. The device of claim 1, wherein said anode and cathode are connected through an external circuit to a D.C. power supply.

3. The device of claim 2, wherein said external circuit contains a resistor.

4. The device of claim 3, wherein said resistor is a variable resistor.

5. The device of claim 2, wherein said external circuit contains a switch.

6. A device for dispensing fluids or semi-fluids where the rate of dispensing is proportional to the electrochemical generation of gas which in turn is proportional to a D.C. current passing through a gas-generating electrochemical cell, and where the gas generating cell utilized is the device claimed in claim 1, comprising:

two adjacent chambers which combined have fixed volume but which share a flexible diaphragm or movable member between them such that as the volume of one chamber increases, the volume of the second chamber decreases;

where gas generated from said electrochemical cell enters and pressurizes the first chamber;

where the second chamber is adapted to be filled with the fluid or semi-fluid to be dispensed; and where the second chamber has an opening through which the fluid or semi-fluid will flow as gas enters the first chamber.

7. A device defined in claim 1 where the separator is a solid polymer electrolyte capable of selectively transporting monovalent metal cations.

8. A device defined in claim 1, wherein the separator is a cation conductive ceramic.

9. A device defined in claim 1 where the cathode includes a reducible metal salt.

10. A device defined in claim 1 where the cathode contains a halogen, chalcogen and mixtures thereof.

11. A device defined in claim 1 where the cathode is gas permeable and reduces oxygen.

12. A device defined in claim 1 where the cathode is gas permeable to evolved hydrogen.

13. A device defined in claim 12 where the oxygen absorber is adapted to release carbon dioxide as oxygen is absorbed so that the net gas stream from the anode is substantially carbon dioxide in larger volume than if only an oxygen absorber were utilized.

14. A device defined in claim 13 where the cathode includes as a constituent $NiCO_3$, $CuCO_3 \cdot Cu(OH)_2$ (malachite), or $2CUCO_3 \cdot Cu(OH)_2$ (azurite).

15. A device defined in claim 1 additionally containing an oxygen absorber in communication with said anode chamber, said absorber adapted to absorb oxygen from the gas evolved from the anode so that the net gas stream from the anode is substantially carbon dioxide.

16. A device defined in claim 1 where the D.C. power source is a battery, capacitor, or solar cell, or combination thereof.

17. A device defined in claim 1 where the anodic current collector is nickel, nickel alloy, nickel oxide, or oxide of nickel alloy or nickel plated steel.

18. A device for electrochemically generating carbon dioxide gas or a mixture of carbon dioxide and oxygen gases in an adjustable quantity proportional to the cell current, comprising:
   an electrochemical cell having a corrosion-resistant container or housing;
   a cathode which includes as a constituent a reducible metal carbonate or basic carbonate and an electronically conductive current collector:
   an anode with hydrophilic and hydrophobic zones with an electronically conductive current collector therebetween, and where the anode structure has perforations to permit gas to be released;
   an ionically conductive, microporous, separator between the anode and cathode; and a direct current (D.C) power source.

19. A substantially sealed device for electrochemically generating carbon dioxide gas or a mixture of carbon dioxide and oxygen gases in an adjustable quantity proportional to the cell current, comprising:
   an electrochetnical cell having a corrosion resistant container or housing;
   a sealed cathode chamber containing a reducible material and an electronically conductive current collector;
   a substantially sealed anode chamber containing an oxidizable material and an electronically conductive current collector wherein said oxidizable material is a metal carbonate, metal bicarbonate, or combination thereof, and wherein the anode chamber structure has perforations or diffusion pores to permit gas to be released;
   an ionically conductive separator between the anode chamber and cathode chamber structured to maintain physical separation of the materials in each chamber; and
   optionally a switch and variable or fixed resistor forming a circuit with said power source and electrochemical cell.

20. A device as defined in claim 19, wherein the metal carbonate is a carbonate of a monovalent metal from the class consisting of sodium, lithium, potassium, rubidium, cesium, silver, and copper and mixtures thereof.

21. A device as defined in claim 19, wherein the metal bicarbonate is a carbonate of a monovalent metal selected from the class consisting of sodium, lithium, rubidium, potassium, cesium, silver, and copper and mixtures thereof.

22. A device defined in claim 21, wherein the solid polymer electrolyte is a laminated composite having a preference for the transport of cations.

23. A device defined in claim 22 where the ceramic is selected from the class consisting of beta-alumina or beta"-alumina ionic conductors in which cations such as sodium, lithium, potassium, rubidium, cesium, silver, or copper ions conduct under the influence of applied potential.

24. A device defined in claim 23 where the ceramic has the formula $Na_{1+x}Zr_xP_{3-x}Si_xO_{12}$ where x has a value of from zero to three.

25. A device defined in claim 22 where the ceramic is a metal ion super conductor electrolyte.

26. A device defined in claim 19 where the cathode includes a reducible metal salt selected from the class consisting of silver sulfate, copper sulfate, copper chloride and copper fluoride.

27. A device defined in claim 26 where the cathode contains iodine, sulfur and mixtures thereof.

* * * * *